United States Patent [19]
Simmonds et al.

[11] Patent Number: 6,013,862
[45] Date of Patent: Jan. 11, 2000

[54] WHEAT ALEURONE REGULATORY ELEMENTS

[75] Inventors: John Simmonds, Nepean; Leslie Cass, Carp; Linda Harris, Greely; Sharon Allard, Nepean, all of Canada

[73] Assignees: Her Majesty in right of Canada, as represented by the Minister of Agriculture; Agri-Food Canada, both of Ottawa, Canada

[21] Appl. No.: 09/102,046

[22] Filed: Jun. 22, 1998

[30] Foreign Application Priority Data

May 7, 1998 [CA] Canada .................................. 2230975

[51] Int. Cl.$^7$ .............................. A01H 1/00; C12N 5/04; C12N 15/09; C12N 15/82
[52] U.S. Cl. .................... 800/287; 435/69.1; 435/320.1; 435/419; 435/420; 435/468; 536/24.1; 800/295; 800/320.3
[58] Field of Search .............................. 435/69.1, 320.1, 435/410, 419, 468; 536/24.1; 800/278, 287, 295, 320.3

[56] References Cited

U.S. PATENT DOCUMENTS 5,525,716  6/1996  Olsen et al. ........................... 536/24.1

FOREIGN PATENT DOCUMENTS

| 2110772 | 6/1995 | Canada | C12N 15/82 |
| WO 95/23230 | 8/1995 | WIPO | C12N 15/82 |

OTHER PUBLICATIONS

Kim et al, Plant Mol. Biol., vol. 24, pp. 105–117, 1994.

Skriver et al, Structure and expression of the barley lipid transfer protein gene Ltp1, Plant Molecular Builogy 18:585–589, 1992.

Dieryck et al, Nucleotide sequence of a cDNA encoding a lipid transfer protein from wheat (*Triticum duram* Desf.), Plant Molecular Builogy, 19:707–709, 1992.

Linnestad et al, Promoter of a Lipid Transfer Protein Gene Expressed in Barley Aleurone Cells Contains Similar myb and myc Recognition Sites as the Maise Bz–McC Allele, Plant Physiol. (1991) 97, 841–843.

Jakobsen et al, Barley aleurone cell development: molecular cloning of aleurone–specific cDNAs from immature grains, Plant Molecular Biology 12:285–93, 1989.

Kalla et al 1994, The promoter of the barley aleurone–specific gene encoding a putative 7KDa lipid transfer protein confers aleurone cell–specific expression in transgenic rice, Plant Journal (1994) 6(6):849–860.

Molina et al, Developmental and pathogen–induced expression of three barley genes encoding lipid transfer proteins, The Plant Journal (1993) 4(6):983–991).

Odell, J.T. et al, Identification of DNA sequences required for activity of the cauliflower mosaic virus 35S promoter, Nature vol. 313–810–812, 1985.

McElroy D., et al Isolation of An Efficient Actin Promoter for use in Rice Transformation, The Plant Cell vol. 2:163–171 (1990).

*Primary Examiner*—Gary Benzion
*Assistant Examiner*—Ashwin Mehta
*Attorney, Agent, or Firm*—Morgan, Lewis & Bockius, LLP

[57] ABSTRACT

This invention is directed to regulatory elements obtained from a wheat aleurone gene LtpW1. The regulatory element, analogs thereof, or truncated derivatives of this regulatory element, can be used to express heterologous genes of interest within the aleurone cells of a plant. This invention is also directed to vectors comprising these regulatory elements operatively linked with a heterologous gene of interest, as well as plant cell cultures and transgenic plants comprising these vectors. A method for the preparation of a plant using the regulatory elements of this invention are also disclosed. Furthermore, this invention is directed to a truncated LtpW1 regulatory element that exhibits constitutive activity within plants.

24 Claims, 11 Drawing Sheets

*SEQ ID NO:1 (687 bp) >

-688 TCTAGAGAAAGAGTTTTAGACCGGAGGTATTTGTTAGGAAGTACTTCTTGCCATACTAGT

-628 TTCAATAAAGTAGCTTGAAAAGACATTTGTTAAGCAACCATGTGTTTTAATATGAAGAT

-568 CCTCAATACCGAGAGCCTTTGGTCCCATGGATGACACAAAACTTCCCACTTGTTTTTTTT

*SEQ ID NO:2 (473 bp) >

-508 TTTTGTGTGTGTGTGGGTAAACTTCCCACTTGGTTAACCTATACTTCCGCTTATGTTCAT

-448 CACTTTGCCAGAAAATTGCATATGTGAAGGAAGTGCCAATATTTAATACCGTCTGGTGTT

-388 ATAAATTCATCTCCCAAAATTATTGGAGTTGAAGATTCACTTGAAAAAATAATTTGACAT

-328 ATTAAAGATGTTGCCCTTGCGCGGGGTATCTGCAAATTGAGGATCCAAGGGACGATTGCA

-268 TCCAGTTCTAAACACACCATTATGATTTCAGTGATAATGCATGCTT*CCAAA*GCCCAGCTG

*SEQ ID NO:3 (206 bp) >

-208 CAAGCTTGGGCCATCCTTCGGAAGGGAAAAAGAAAAAGGGGTCCTGCTGCACCAGCGACT

-148 AAACCATCCACGCATCTCTCGCTCGAACCCC*TATTTAA*GCCCCTCCATTCTTCCCTACAT

-88 TCTCC*ACACAA*CCACGAGTTGCTCATCTCTCCACCCAATCATCACTAGCTAATACGGTGC

*+1

-28 ACTGTTAGCTACAGACCAAGAAGTGATCATGGCCCGCGCTCAGGTAATGCTCATGGCCGT

33 CGCCTTGGTGCTCATGCTCGCGGCGGTCCCGCGCGCTGCCGTGGCCATCGACTGCGGCCA

93 CGTTGACAGCTTGGTGAGACCCTGCCTGAGCTACGTTCAGGGCGGCCCCGGCCCGTCTGG

153 GCAGTGCTGCGACGGCGTCAAGAACCTCCATAACCAGGCGCGATCCCAGAGCGATCGCCA

213 AAGCGCTTGCAACTGCCTCAAGGGGATCGCTCGTGGCATCCACAATCTCAACGAGGACAA

273 CGCCCGCAGCATCCCCCCCAAGTGCGGTGTCAACCTCCCATACACCATCAGTCTCAACAT

333 CGACTGCAGCAGGTGATTAATTCACATGCAAGCATATATATATGAACACTCATCCACGTA

393 AAATTTATTGATATTAACATTAATCAAATCTTTGCACTGCAGGGTGTAATGGGCGACGAT

453 CCGTCAAGCTGGTGCTCAGCTCATCCATCCACGTGGAGTTGAAGCGCGCAGCCTCTATCC

513 CTATGTAGTATGGTCACTAGTTATGCGAGTTTATACTGAATATGAATAAGAACTCTCTCC

573 AGCTGGCTTGCTGGTACTCCTCTGGAGGAGATCAGTATCTGTGTACCTGAGAGTTGAGAG

633 TTTGTACCATGGGCACTCCCAGTGTTTATGGACTTTAATACATACAACTCGTTCTGTTCA

693 GCGTGTGACTTATCTTTGTTTCCTCACGTTCGCCTGTCATATACTCCTTCCATCCGGTAT

753 TAGTTGGCGTTCAAACGGATATATCTAGA

FIGURE 3

```
-679 GTTTTAGACCGGAGGTATTTGTTAGGAAGTACTTCTTGCCATACTAGTTTCAATAAAGTA
     |||| | | | || |    |   |    |       || |    |||
-700 GTTTGATAACAAAGTAGTAAAAAACTAAAGTATTAAAAACTGCAGTAATTTTACGTGTA

-619 GCTTGAAAAGACATTTGTTAAGCAACCATGTGTTTTAATATGAAGATCCTCAATACCGA
     | | |||||| ||  | |||    | ||   |||| | |    |    || ||
-630 GATAGAAAATACCATGGTTTTAATATAATAATATTTTTGCAGTATTCACAATGTAGAGA

-559 GAGCCTTTGGTCCCATGGATGACACAAAACT..............................
     |   |||| | |       |
-570 AACTGTTTGATTACGCCACATATTACTGCAGTTTAGATCGAGCAAGTACACGGGAAGAAG

-528 .........TCCCACTTGTTTTTTTTTTTGTGTGTGTGTGGGTAAACTTCCCACTTGGT
              ||||||  || ||||     |      | |   ⊢||    |     | |
-510 ATAACGACGTCCCACCCCTTCTTTTCGCCTTCTCTGTTTTTAAAAGAGGTCTGGGGTT

-477 TAACCTATACTTCCGCTTATGTTCATCACTTTGCCAGAAAATTGCATATGTGAAGGAAGT
     | |    | |     ||| |     |         | |   |       |      | |
-450 AGTTTTTTCAATACTGCAGTTTTAAAATCACAATTCTTAGAGGCAACCAAACACCTCATT

-417 GCCAATATTTAATACCGTCTGGTGTTATAAATTCATCTCCCAAAATTATTGGAGTTGAAG
     |  ||||       |         |     || |||||    |
-390 GTAAATAAAACTATGATAATCTCCAAAACTGCAGTATTCTAAAAATACTAC..........

-357 ATTCACTTGAAAAAATAATTTGACATATTAAAGATGTTGCCCTTGCGCGGGGTATCTGCA
             ||||||  ||||  ||  | ||    |                    |  ||
-339 ..........AAAATTCTTTGTTATCAAACAGGGCCTAAGGAGTTAAAAAAATTTAGCC

-297 AATTGAGGATCCAAGGGACGATTGCATC.....CAGTTCTAAACACACCATTATGATTTC
         |   |   | |||  |           ||||  |  ||||||      ||||
-289 GTAACTGAGACTCGGCGAGGCACCAGCAGCTAGCAGTCATCAACACT......TGATGGT
                                    *SEQ ID NO:3 >
-242 AGTGATAATGCATGCTTCCAAAGCCCAGCTGCAAGCTTGGGCCATCCTTCGGAAGGGAAA
     |  |   |     |   |    |  |    |       |  ||      | |       |
-235 TGGCAAAGGCGAGTCGACGTGTCGCGGGGCTCGGCCTGAGCGGGAGATACAATCTGTTCT

-182 AAGAAAAAGGGGTCCTGCTGCACCAGCGACTAAACCATCCACGCATCTCTCGCTCGAACC
           ||    |||    ||  ||   ||||||||  ||||||  ||||||||||||||||||||
-175 CCAGTAACCCCGTCGATTTGGCCCGCCGACTAAAGCATCCAGGCATCTCTCGCTCGAACC

-122 CCTATTTAAGCCCCTCCATTCTTCCCTACATTCTCCACACAACCACGAGTTGCTCATCTC
     |||||||||||||||||||||||||  ||||  |||||||||||||      ||||||||||
-115 CCTATTTAAGCCCCTCCATTCCTCCCAACATTCTCCACACCTCCACGAGTTGC.......
                                                                    *
 -62 TCCACCCAATCATCACTAGCTAATACGGTGCACTGTTAGCTACAGACCAAGAAGTGATCA
     |||||||||||||  |||| || |||||||||||||| ||||||||||||  |||||||||||
 -53 .........TCATCACTAGCTAGTACGTTGTACTGTTAGCTACAGATTAAGAAGTGATCA
```

FIGURE 4a

```
  2 TGGCCCGCGCTCAGGTAATGCTCATGGCCGTCGCCTTGGTGCTCATGCTCGCGGCGGTCC
    ||||||||||||||||| |||||||||||| |||||||||||| |||||| |||||| ||
  2 TGGCCCGCGCTCAGGTACTGCTCATGGCCGCCGCCTTGGTGCTGATGCTCACGGCGGCCC

62 CGCGCGCTGCCGTGGCCATCGACTGCGGCCACGTTGACAGCTTGGTGAGACCCTGCCTGA
    |||||||||||||||||| || |||||||||| ||||||||| | ||| ||| |||||||
 62 CGCGCGCTGCCGTGGCCCTCAACTGCGGCCAGGTTGACAGCAAGATGAAACCTTGCCTGA

122 GCTACGTTCAGGGCGGCCCCGGCCCGTCTGGGCAGTGCTGCGACGGCGTCAAGAACCTCC
    |||||||||||||||||||||||||| || | ||||||| |||||||||| | | ||||
122 CCTACGTTCAGGGCGGCCCCGGCCCGTCCGGCGAATGCTGCAACGGCGTCAGGGATCTCC

182 ATAACCAGGCGCGATCCCAGAGCGATCGCCAAAGCGCTTGCAACTGCCTCAAGGGGATCG
    |||||||||||| |||| | |||| |||||||| || |||||||||||| |||||||||
182 ATAACCAGGCGCAATCCTCGGGCGACCGCCAAACCGTTTGCAACTGCCTGAAGGGGATCG

242 CTCGTGGCATCCACAATCTCAACGAGGACAACGCCCGCAGCATCCCCCCCAAGTGCGGTG
    |||| |||||||||||||||||||   |||||||| ||||||||||| |||||||||  ||
242 CTCGCGGCATCCACAATCTCAACCTCAACAACGCCGCCAGCATCCCCTCCAAGTGCAATG

302 TCAACCTCCCATACACCATCAGTCTCAACATCGACTGCAGCAGGTGATTAATTCACATGC
    ||||| ||||||||||||||||| | | |||||||||||| ||||||||||| ||||| |
302 TCAACGTCCCATACACCATCAGCCCCGACATCGACTGCTCCAGGTGATTAAATTTACACT

362 AAGCATA........................TATATATGAAC
    | |                                |||||| ||||
363 CATCCAGAGTGAAATCTTTAAAAAGAACTATATTTACGAACGGAGTGAGTATATAGGAAC

380 ACTCATCCACGTAAAATTTATTGATATTAACATTAATCAAATCTTTGCA.CTGCAGGGTG
    | ||||||||||||||||| |||||||||||||||||  | ||| |||||| |
423 ATTCATCCACGTAAAATTTGTTGATATTAACATTAACACGCATGATTGACCTGCAGGATT

440 TAATGGGCGACGATCCGTCAAGCTGGTGCTCAGCTCATCCATCCACGTGGAGTTGAAGCG
    || || ||||||||||||||||||||||||||||||||||| |||||||||||| |||||||
483 TACTGAGCGACGATCCGTCAAGCTGGTGCTCAGCTCATCGATCCACGTGGAGCTGAAGCG

500 CGCAGCCTCTATCCCTATGTAGTATGGTCACTAGTTATG.CGAGTTTATACTGAATATGA
    ||||||||| ||||||||||||||||| || ||||||| |||||||||| ||||
543 CGCAGCCTCTGTCCCTATGTAGTATGGCTACCAGTTATGCCGAGTTTATGCTGA......

559 ATAAGAACTCTCTCCAGCTGGCTTGCTGGTACTCCTCTGGAGGAGATCAGTATCTGTGTA
    |||||||||||||||           |||||||| |||||||||||||||||||||| ||||
597 ATAAGAACTCTCTCCT...........GTACTCCTTTGGAGGAGATCAGTATCTATGTA

619 CCTGAGAGTTGAGAGTTTGTACCATGGGCACTCCCAGTGTTTATGGACTT
    | |||||||||||||||||||||||| ||||||||||||||||||||||||
645 CGTGAGAGTTGAGAGTTTGTACCATCGGCACTCCCAGTGTTTATGGACTA
```

FIGURE 4a1

```
-681  AAAGAGTTTTAGACCGGAGGTATTTGTTAGGAAGTACTTCTTGCCATACTAGT..TTCAA
       ||         |  ||    ||     || ||      ||        |||   |||||
-822  AACCGTGGCCTAAAAATAAGCCGATGAGGATAAATAAAATGTGGTGGTACAGTACTTCAA

-623  TAAAGTAGCTTGAAAAGACATTTGTTAAGCAACCATGTGTTTTAATATGAAGATCCTCA
         |   ||    ||||    |  ||   |   |   |  |          || |
-762  GAGGTTTACTCATCAAGAGGATGCTTTTCCGATGAGCTCTAGTAGTACATCGGACCTCAC

-563  ATACCGAGAGCCTTTGGTCCCATGGATGACACAAAACTTCCCACTTGTTTTTTTTTTTG
      |||||    |     |     ||    | ||      |     |    ||||  ||| ||
-702  ATACCTCCATTGTGGTGAAATATTTTGTGCTCATTTAGTGATGGGTAAATTTTGTTTATG

-503  TGTGTGT..GTGGGTAAACTTCCCACTTGGTTAACCTATACTTCCGCTTATGTTCATCAC
          |  | ||    | | |||    |||    |  ||   ||-  | ||  |      ||
-642  TCACTCTAGGTTTTGACATTTCAGTTTTGCCACTCTTAGGTTTTGACAAATAATTTCCAT

-445  TTTGCC.....AGAAAATTGCATATGTGAAGGAAGTGCCAATATTTAATACCGTCTGGTG
         |  ||         || |||    | | |      | |||  | ||  |        ||
-582  TCCGCGGCAAAAGCAAAACAATTTTATTTTACTTTTACCACTCTTAGCTTTCACAATGTA

-390  TTATAAATTCATCTCCCAAAATTATTGGAGTTGAAGATTCACTTGAAAAAATAATTTGAC
        |  |||||  |   |||      |||||   ||    ||        |  ||||||||| |     | ||
-522  TCACAAATGCCACTCTAGAAATTC.TGTTTATGCCACAGAATGTGAAAAAAAACACTCAC

-330  ATATTA......AAGATGTTGCCCTTGCGCGGGGTATCTGCAAATTGAGGATCCAAGGGA
         ||||      |||  ||||        |              ||| |  |  ||              |
-463  TTATTTGAAGCCAAGGTGTTCATGGCATGGAAATGTGACATAAAGTAACGTTCGTGTATA

-276  CGATTGCATCCAGT...TCTAAACACACCATTATGATTTCAGTGATAATGCATGCTTCCA
         ||   ||        ||   ||||      |       |  |||       | | |||   |
-403  AGAAAAAATTGTACTCCTCGTAACAAGAGACGGAAACATCATGAGACAATCGCGTTTGGA
                  *SEQ ID NO:3 >
-219  AAGCCCAGCTGCAAGCTTGGGCCATCCTTCGGAAGGGAAAAAGAAAAAGGGGTCCTGCTG
         | ||    ||  ||     ||||    || |         |||  ||                 ||   |||        ||
-343  AGGCTTTGCATCACCTTTGGATGATGCGCATGAATGG..........AGTCGTCTGCTTG

-159  CACCAGCGACTAAACCATCCACGCATCTCTCGCTCGAACCCCTATTTAAGCCCCTCCATT
         |              |||   ||||    |      |    ||       |||    | ||      |   |    ||
-293  CTAGCCTTCGCCTACCGCCCACTGAGTCCGGGCGGCAACTACCATCGGCGAACGACCCAG

-99  CTTCCCTACATTCTCCACACAACCACGAGTTGCTCATCTCTCCACCCAATCATCACTAG.
         ||   |||    |        ||   ||          ||||||           ||     |   |                ||
-233  CTGACCTCTACCGACCGGACTTGAATGCGCTACCTTCGTCAGCGACGATGGCCGCGTACG

............................................................

-173  CTGGCGACGTGCCCCCGCATGCATGGCGGCACATGGCGAGCTCAGACCGTGCGTGGCTGG
```

FIGURE 4b

```
 -40                             ..................CTAATACGGTGCACTGTTAGCTA
                                                    || | ||     ||||  ||
-113   CTACAAATACGTACCCCGTGAGTGCCCTAGCTAGAAACTTACACCTGCAACTGCGAGAGC

*
 -17   CAGACCAAGAAGTGATCATG
       ||       || |||
 -53   GAGCGTGTGA.GTGTAGCCGAGTAGATCACCGTACGACGACGACGAGGGGCATG
```

FIGURE 4b1 a) p687LtpW1-GUS
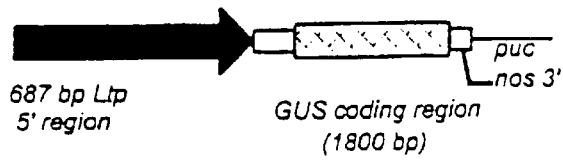
b) p473LtpW1-GUS
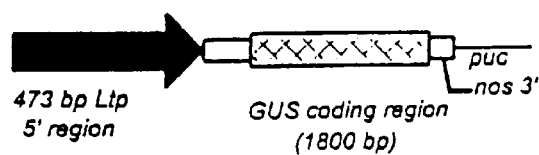
c) p206LtpW1-GUS
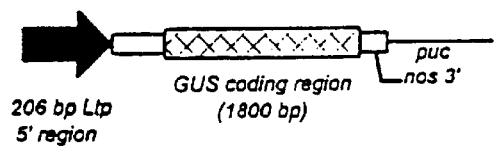
In all three constructs, the ADH1S6 intron lies between The LtpW1 promoter and the GUS coding region.
d) pLC-GUS
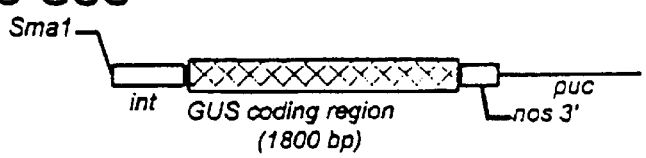
FIGURE 5 a) p35S-GUS
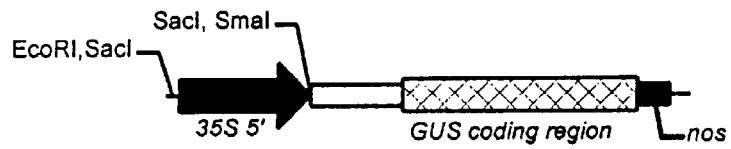
The ADH1S intron lies between the promoter and the GUS gene.
b) pAct-GUS
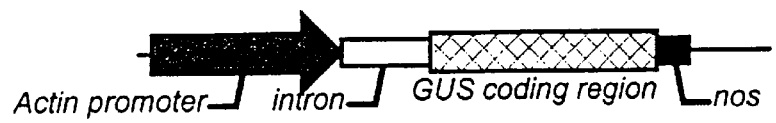
FIGURE 6

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 687 base pairs
      (B) TYPE: nucleic acid
      (C) STRANDEDNESS: single
      (D) TOPOLOGY: linear (ii) MOLECULE TYPE: DNA (genomic)

```
     (vii) IMMEDIATE SOURCE:
           (B) CLONE: LtpW1

(ix) FEATURE:
           (A) NAME/KEY: regulatory element
           (B) LOCATION:1..687

(xi) SEQUENCE DESCRIPTION: SEQ ID NO: 1:

CTAGAGAAAG AGTTTTAGAC CGGAGGTATT TGTTAGGAAG TACTTCTTGC CATACTAGTT    60

TCAATAAAGT AGCTTGAAAA GACATTTGTT AAGCAACCAT GTGTTTTTAA TATGAAGATC   120

CTCAATACCG AGAGCCTTTG GTCCCATGGA TGACACAAAA CTTCCCACTT GTTTTTTTTT   180

TTTGTGTGTG TGTGGGTAAA CTTCCCACTT GGTTAACCTA TACTTCCGCT TATGTTCATC   240

ACTTTGCCAG AAAATTGCAT ATGTGAAGGA AGTGCCAATA TTTAATACCG TCTGGTGTTA   300

TAAATTCATC TCCCAAAATT ATTGGAGTTG AAGATTCACT TGAAAAAATA ATTTGACATA   360

TTAAAGATGT TGCCCTTGCG CGGGGTATCT GCAAATTGAG GATCCAAGGG ACGATTGCAT   420

CCAGTTCTAA ACACACCATT ATGATTTCAG TGATAATGCA TGCTTCCAAA GCCCAGCTGC   480

AAGCTTGGGC CATCCTTCGG AAGGGAAAAA GAAAAAGGGG TCCTGCTGCA CCAGCGACTA   540

AACCATCCAC GCATCTCTCG CTCGAACCCC TATTTAAGCC CCTCCATTCT TCCCTACATT   600

CTCCACACAA CCACGAGTTG CTCATCTCTC CACCCAATCA TCACTAGCTA ATACGGTGCA   660

CTGTTAGCTA CAGACCAAGA AGTGATC                                     687

(2) INFORMATION FOR SEQ ID NO: 2:

(i) SEQUENCE CHARACTERISTICS:
            (A) LENGTH: 473 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: LtpW1

(ix) FEATURE:
            (A) NAME/KEY: regulatory element
            (B) LOCATION:1..473

(xi) SEQUENCE DESCRIPTION: SEQ ID NO: 2:

AACCTATACT TCCGCTTATG TTCATCACTT TGCCAGAAAA TTGCATATGT GAAGGAAGTG    60

CCAATATTTA ATACCGTCTG GTGTTATAAA TTCATCTCCC AAAATTATTG GAGTTGAAGA   120

TTCACTTGAA AAAATAATTT GACATATTAA AGATGTTGCC CTTGCGCGGG GTATCTGCAA   180

ATTGAGGATC CAAGGGACGA TTGCATCCAG TTCTAAACAC ACCATTATGA TTTCAGTGAT   240

AATGCATGCT TCCAAAGCCC AGCTGCAAGC TTGGGCCATC CTTCGGAAGG GAAAAAGAAA   300

AAGGGGTCCT GCTGCACCAG CGACTAAACC ATCCACGCAT CTCTCGCTCG AACCCCTATT   360

TAAGCCCCTC CATTCTTCCC TACATTCTCC ACACAACCAC GAGTTGCTCA TCTCTCCACC   420

CAATCATCAC TAGCTAATAC GGTGCACTGT TAGCTACAGA CCAAGAAGTG ATC         473

(2) INFORMATION FOR SEQ ID NO: 3:

(i) SEQUENCE CHARACTERISTICS:
            (A) LENGTH: 206 base pairs
            (B) TYPE: nucleic acid
            (C) STRANDEDNESS: single
            (D) TOPOLOGY: linear (ii) MOLECULE TYPE: DNA (genomic)
```

(vii) IMMEDIATE SOURCE:
    (B) CLONE: LtpW1

(ix) FEATURE:
    (A) NAME/KEY: regulatory element
    (B) LOCATION:1..206

(xi) SEQUENCE DESCRIPTION: SEQ ID NO: 3:

```
AGCTTGGGCC ATCCTTCGGA AGGGAAAAAG AAAAAGGGGT CCTGCTGCAC CAGCGACTAA      60

ACCATCCACG CATCTCTCGC TCGAACCCCT ATTTAAGCCC CTCCATTCTT CCCTACATTC     120

TCCACACAAC CACGAGTTGC TCATCTCTCC ACCCAATCAT CACTAGCTAA TACGGTGCAC     180

TGTTAGCTAC AGACCAAGAA GTGATC                                          206
```

(2) INFORMATION FOR SEQ ID NO: 4:

(i) SEQUENCE CHARACTERISTICS:
      (A) LENGTH: 1469 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:
      (B) CLONE: LtpW1

(ix) FEATURE:
      (A) NAME/KEY: regulatory element
      (B) LOCATION:1..687

(xi) SEQUENCE DESCRIPTION: SEQ ID NO: 4:

```
TCTAGAGAAA GAGTTTTAGA CCGGAGGTAT TTGTTAGGAA GTACTTCTTG CCATACTAGT      60

TTCAATAAAG TAGCTTGAAA AGACATTTGT TAAGCAACCA TGTGTTTTTA ATATGAAGAT     120

CCTCAATACC GAGAGCCTTT GGTCCCATGG ATGACACAAA ACTTCCCACT TGTTTTTTTT     180

TTTTGTGTGT GTGTGGGTAA ACTTCCCACT TGGTTAACCT ATACTTCCGC TTATGTTCAT     240

CACTTTGCCA GAAAATTGCA TATGTGAAGG AAGTGCCAAT ATTTAATACC GTCTGGTGTT     300

ATAAATTCAT CTCCCAAAAT TATTGGAGTT GAAGATTCAC TTGAAAAAAT AATTTGACAT     360

ATTAAAGATG TTGCCCTTGC GCGGGGTATC TGCAAATTGA GGATCCAAGG GACGATTGCA     420

TCCAGTTCTA AACACACCAT TATGATTTCA GTGATAATGA ATGCTTCCAA AGCCCAGCTG     480

CAAGCTTGGG CCATCCTTCG AAGGGAAAAA AGAAAAAGGG GTCCTGCTGC ACCAGCGACT     540

AAACCATCCA CGCATCTCTC GCTCGAACCC CTATTTAAGC CCCTCCATTC TTCCCTACAT     600

TCTCCACACA ACCACGAGTT GCTCATCTCT CCACCCAATC ATCACTAGCT AATACGGTGC     660

ACTGTTAGCT ACAGACCAAG AAGTGATCAT GGCCCGCGCT CAGGTAATGC TCATGGCCGT     720

CGCCTTGGTG CTCATGCTCG CGGCGGTCCC GCGCGCTGCC GTGGCCATCG ACTGCGGCCA     780

CGTTGACAGC TTGGTGAGAC CCTGCCTGAG CTACGTTCAG GGCGGCCCCG GCCCGTCTGG     840

GCAGTGCTGC GACGGCGTCA AGAACCTCCA TAACCAGGCG CGATCCCAGA GCGATCGCCA     900

AAGCGCTTGC AACTGCCTCA AGGGGATCGC TCGTGGCATC CACAATCTCA CGAGGACAA     960

CGCCCGCAGC ATCCCCCCCA AGTGCGGTGT CAACCTCCCA TACACCATCA GTCTCAACAT    1020

CGACTGCAGC AGGTGATTAA TTCACATGCA AGCATATATA TATGAACACT CATCCACGTA    1080

AAATTTATTG ATATTAACAT TAATCAAATC TTTGCACTGC AGGGTGTAAT GGGCGACGAT    1140

CCGTCAAGCT GGTGCTCAGC TCATCCATCC ACGTGGAGTT GAAGCGCGCA GCCTCTATCC    1200

CTATGTAGTA TGGTCACTAG TTATGCGAGT TTATACTGAA TATGAATAAG AACTCTCTCC    1260

AGCTGGCTTG CTGGTACTCC TCTGGAGGAG ATCAGTATCT GTGTACCTGA GAGTTGAGAG    1320
```

```
TTTGTACCAT GGGCACTCCC AGTGTTTATG GACTTTAATA CATACAACTC GTTCTGTTCA    1380

GCGTGTGACT TATCTTTGTT TCCTCACGTT CGCCTGTCAT ATACTCCTTC CATCCGGTAT    1440

TAGTTGGCGT TCAAACGGAT ATATCTAGA                                      1469
```

WHEAT ALEURONE REGULATORY ELEMENTS

CROSS REFERENCES TO RELATED APPLICATIONS

This application claims priority to a Canadian Patent Application filed on May 7, 1998 Application No. 2,230,975, the application of which is hereby incorporated by reference in its entirety.

BACKGROUND OF THE INVENTION

The present invention relates to plant gene regulatory elements and their use in the expression of genes of interest. More specifically, the present invention relates to the use of aleurone regulatory elements for organ and tissue specific expression of a gene of interest within aleurone tissues of plants.

The endosperm of a seed is the site of deposition of storage products such as starch and proteins used by the developing embryo during germination. The endosperm surrounds the embryo of developing and mature cereal seeds. The endosperm comprises a peripheral layer of aleurone cells, which are specialized secretory cells. During germination, the aleurone layer is involved in the transfer of metabolites from the transport system to the endosperm. Furthermore, several antimicrobial compounds required to protect the seed during dormancy, imbibition and germination are synthesized within this tissue. The aleurone cells differentiate from primary endosperm cells 10–21 days after fertilization.

Several aspects of hormonal regulation of gene transcription within aleurone tissue, in germinating barley seeds have been well characterized (Fincher 1989, Annu. Rev. Plant Physiol. Mol. Biol. 40:305–346). For example, genes encoding α-amylase, responsible for the digestion of the starch stored within the starchy endosperm, and β-glucanase, which digests the cell walls, have been isolated and characterized (WO 90/01551 Rogers; U.S. Pat. No. 5,677,474 Rogers, issued Oct. 14, 1997; Karrer et al 1991, Plant Mol. Biol.16:797–805; Slakeski and Fincher 1992). Furthermore, several structural and regulatory genes involved in anthocyanin biosynthesis within the aleurone have been isolated and characterized (Paz-Ares et al 1987, EMBO J. 5:829–833; Dellaporta et al 1988, pp263–282 18th Stadler Genet. Symp. ed. J. P. Gustafsant and R.Appels). Other genes representing differentially expressed transcripts within aleurone layers have also been reported including CHI26 (Lea et al 1991, J. Biol. Chem. 266:1564–73); pZE40 (Smith et al 1992, Plant Mol. Biol. 20:255–66); pHvGS-1, and pcHth3 (Heck and Ho 1996, Plant Mol. Biol. 30:611–23). Several genes encoding lipid transfer proteins (Ltp) have also been obtained from barley aleurone tissues, including B11E- barley Ltp1, and B12A- barley Ltp2 (Jakobsen et al 1989, Plant Mol. Biol. 12: 285–93). Only one of these genes, B12A, has been expressed ectopically in transgenic plants. In this case the regulatory element is active only during seed development (Kalla et al 1994 Plant J. 6:849–860)

Lipid transfer proteins are responsible for the transfer of phospholipids between membranes in vitro, and likely play a role during membrane biogenesis. This may be especially important in aleurone cells which are known to develop extensive membrane systems. Skriver et al (1992, Plant Mol.Biol. 18: 585–589) disclose the sequence of a genomic Ltp (Ltp1), including the promoter region, from barley. Northern analysis demonstrated that this gene was specifically expressed in developing and germinating seeds, as well as in whole seeds and aleurone layers obtained from seeds 30 days post anthesis (dpa). No expression of Ltp1 mRNA was observed in root, leaf, or shoot tissues, or coleoptiles of germinating seeds. Linnestad et al (1991, Plant Physiol 97: 841–843) also discloses the promoter sequence of the Ltp1 regulatory element from barley which was obtained using barley cDNA B 12A as a probe. The Ltpl promoter, as well as a modified form of this promoter is disclosed in WO 95/23230 (Feb. 23, 1995; Olsen et al). The modified form of the Ltp1 promoter was not specific to directing expression within aleurone cells, and was active in a range of plant organs and tissues including aleurone cells, scutellar epithelial tissue and vascular tissue during germination or in the plant, including root, leaves and stem.

The promoter of B 12A (also termed Ltp2) directs expression specifically within the aleurone layer of developing grain as determined using transgenic cereal plants (Kalla et al 1994, Plant J. 6: 849–860). The sequence of the Ltp2 promoter is disclosed in CA 2,110,772 (filed Dec. 6, 1993, Olsen and Kalla) and U.S. Pat. No. 5,525,716 (Kalla et al). Dieryck et al (1992, Plt. Molec. Biol. 19:707–709) disclose the incomplete cDNA sequence of a wheat (*Triticum durum*) Ltp (pTd4.90). Ltp genes comprise a multigenic family and are ubiquitous in plants. Unfortunately as these genes or corresponding proteins have been isolated from various species there is no uniformity in the terminology used to identify the genes. Hence Ltp1 from tobacco, barley and Arabidopsis are not the same. As well, two barley Ltp2 genes are described in the literature; barley Lpt2 as described in Molina and Garcia-Olmedo (Plant J. 4:983–991) is a leaf Lpt, while barley Ltp2 as described in Kalla et al (1994 Plant J. 6:849–860) is aleurone specific.

It is desirable to provide regulatory elements capable of controlling aleurone specific expression that is not detrimental to the developing embryo and seedling. Aleurone-specific regulatory elements may be used for the regulation of the expression of heterologous or native genes within aleurone tissue of cereal seeds in order to modify grain development and germination. For example, placing genes of interest under the control of aleurone-specific regulatory elements may be used to:

1) mediate the unloading of metabolites from the transport system into the endosperm, since this metabolite unloading is processed through aleurone cells. By expressing genes of interest involved in this process specifically within the aleurone, the grain yield may be affected. For example, which is not to be considered limiting in any manner, these genes of interest may include $Na^+$ and $K^+$ ATPases finctioning in active transport, modifiers of membrane pore exclusion parameters such as TMV movement proteins, invertase for sucrose transport etc.;

2) affect the quality of the grain, through the production of specific proteins or enzymes, lipids, secondary metabolites etc. and their secretion into the endosperm during endosperm development or endosperm digestion. For example, which is not to be considered limiting in any manner, such proteins may include starch synthase, ADP glucose pyrophosphorylase, monoclonal antibodies, glutenins, anticoagulants (eg hirudin), anti-pathogenic phenolics etc.. Furthermore, expression of a gene of interest within the aleurone may also be used in order to express proteins for nutritional or medicinal purposes for feeding to animals or humans;

3) regulate pre-harvest sprouting by affecting dormancy, for example which is not to be considered limiting, by over-expression of ACC synthase to induce inhibitory levels of ethylene;

4) enhance alcohol production- introduction of novel high temperature resistant enzymes for industrial application, including, but not limited to, thermostable amylases, pectinases and invertase;

5) modify disease resistance of developing and germinating grains by expressing proteins, for example but not limited to, oxalate oxidase, glucose oxidase, chitinase, or lipid transfer proteins, in combination with a suitable signal peptide for targeting to the extracellular matrix and cell wall localization. This approach can be used to modify the matrix to provide a stronger physical barrier against invading pathogens or to direct specific anti-pathogen agents to the aleurone/pericarp interface.

This invention characterizes novel wheat aleurone specific regulatory elements active during embryo development and germination and which control expression of heterologous genes of interest within transgenic plants.

SUMMARY OF THE INVENTION

The present invention relates to plant gene regulatory elements and their use in the expression of genes of interest. More specifically, the present invention relates to the use of aleurone regulatory elements for stage and tissue specific expression of a gene of interest within aleurone tissues of plants.

According to the present invention there is provided an isolated DNA molecule that is substantially homologous to the nucleotide sequence of SEQ ID NO:1. Furthermore, this invention is directed to an isolated DNA molecule comprising an XbaI-BclI fragment, a HincIII-BclI fragment, or a HindIII-BclI fragment, as defined herein.

The present invention also provides for an isolated DNA molecule comprising at least 40 contiguous nucleotides of the nucleotide sequence of SEQ ID NO: 1. Also considered as part of this invention is an isolated DNA molecule that comprises the nucleotide sequence of SEQ ID NO: 1.

Furthermore, this invention provides for an isolated DNA molecule comprising at least 21 contiguous nucleotides of the nucleotide sequence comprising nucleotides 1–481 of SEQ. ID NO: 1, an isolated DNA molecule comprising at least 19 contiguous nucleotides of the nucleotide sequence comprising nucleotides 1–214 of SEQ ID NO: 1, an isolated DNA molecule comprising nucleotides 1–481 of the nucleotide sequence of SEQ ID NO:1, an isolated DNA molecule comprising nucleotides 1–214 of the nucleotide sequence of SEQ ID NO:1, or an isolated DNA molecule comprising nucleotides 215–481 of the nucleotide sequence of SEQ ID NO: 1.

This invention is also directed to an isolated DNA molecule that is substantially homologous to the nucleic acid sequence of SEQ ID NO:2. Furthermore, this invention is directed to an isolated DNA molecule comprising the nucleotide sequence of SEQ ID NO:2.

This invention also encompasses an isolated DNA molecule that is substantially homologous to the nucleic acid sequence of SEQ ID NO:3. This invention also includes an isolated DNA molecule comprising the nucleotide sequence of SEQ ID NO:3.

Also included within this invention is a vector comprising an isolated DNA molecule, comprising a nucleic acid substantially homologous to nucleotide sequence of SEQ ID NO: 1, and a gene of interest operatively linked thereto, wherein the isolated DNA molecule controls the expression of a gene of interest.

This invention is also directed to a vector, comprising an isolated DNA molecule comprising at least 40 contiguous nucleotides of the nucleotide sequence of SEQ ID NO:1, or 21 contiguous nucleotides of the nucleotide sequence comprising nucleotides 1–481 of SEQ ID NO:1, or 19 contiguous nucleotides of the nucleotide sequence comprising nucleotides 1–214 of SEQ ID NO:1, and a gene of interest operatively linked thereto. This invention also embraces a vector comprising nucleotides 1–481 of the nucleotide sequence of SEQ ID NO:1, nucleotides 1–214 of the nucleotide sequence of SEQ ID NO: 1, or nucleotides 215–481 of the nucleotide sequence of SEQ ID NO: 1. Furthermore, this invention provides for a vector comprising the nucleotide sequence of SEQ ID NO:1, SEQ ID NO:2, SEQ ID NO:3, or SEQ ID NO:4, controlling the expression of a gene of interest operatively linked thereto.

This invention also includes a transformed plant cell culture comprising a vector as defined above.

This invention is also directed to a transgenic plant transformed with a vector as defined above.

Also considered an aspect of this invention is a method of expressing a gene of interest within aleurone of a plant comprising;

i) operatively linking a gene of interest for which expression is desired with a regulatory element obtained from wheat aleurone to produce a chimeric gene construct; and ii) introducing the chimeric gene construct into the plant; wherein the regulatory element comprises the nucleotide sequence substantially homologous to the nucleotide sequence of SEQ ID NO: 1.

This invention also includes the method as described above, wherein the regulatory element comprises the nucleotide sequence containing at least 21 contiguous nucleotides of the nucleotide sequence comprising nucleotides 1–481 of SEQ ID NO:1, 19 contiguous nucleotides of the nucleotide sequence comprising nucleotides 1–214 of SEQ ID NO: 1, or comprising nucleotides 1–481 of the nucleotide sequence of SEQ ID NO: 1, nucleotides 1–214 of the nucleotide sequence of SEQ ID NO: 1, or nucleotides 215–481, or comprising the nucleotide sequence of SEQ ID NO: 1, SEQ ID NO: 1, SEQ ID NO: 2, SEQ ID NO:3, or SEQ ID NO:4.

This invention also embraces a constitutive regulatory element obtained from wheat aleurone, characterized in that the constitutive regulatory element is a truncated form of a native regulatory element, LtpW1, and lacks tissue and stage dependant regulation associated with the native regulatory element LtpW1.

The nucleotide sequence of the LtpW1 regulatory element as disclosed herein is different from the barley Ltp1 or 2 regulatory elements, as is the range of activity of the LtpW1 regulatory element. Furthermore, the activity of the truncated LtpW1 regulatory element within the aleurone, relative to barley Ltp2 (Kalla et al 1994, Plant. J. 6: 849–860), is stronger.

BRIEF DESCRIPTION OF THE DRAWINGS

These and other features of the invention will become more apparent from the following description in which reference is made to the appended drawings wherein:

FIG. 1(a) shows *Hordeum vulgare* at 20 dpa; FIG. 1(b) shows *Triticum aestivum* at 10 dpa; FIG. 1(c) shows *T. aestivum* at 20 dpa; FIG. 1(d) shows *T. tungidum* at 10 dpa.

FIG. 2(a) and FIG. 2(b) show 73h germinating wheat grain, and FIG. 2(c) and FIG. 2(d) show 18 dpa developing wheat grain. FIG. 2(a) and FIG. 2(c) show hybridization results using anti-sense probe; FIG. 2(b) and FIG. 2(d) show hybridization with sense probe.

FIG. 3 shows the DNA sequence of the genomic LtpW1 gene. The coding region is underlined (the intron is not underlined). The ATG start and TGG stop codon are in bold type. The cap site, TATA, CAT boxes are italicized and double-underlined at positions −83, −117 and −222, respectively. SEQ ID NO 1 runs from −687 to −1, SEQ ID NO 2 runs from −473 to −1, and SEQ ID NO 3 runs from −206 to −1.

FIG. 4(A–B) shows the DNA sequence alignment of LtpW1 and barley Ltp genes. FIG. 4(a) shows alignment of LtpW1 (top row) and barley Ltp1 (bottom row); FIG. 4(b) shows alignment of LtpW1 (top row) and barley Ltp2 (Kalla et al 1994 Plant J. 6:849–860). The ATG of the Ltp genes is overlined.

FIG. 5(A–D) shows the LtpW1 regulatory element constructs, in all three constructs the ADH1S6 intron lies between the LtpW1 regulatory element and the coding region of the marker gene, GUS. FIG. 5(a) p687LtpW1GUS; FIG. 5(b) p473LtpW1-GUS; FIG. 5(c) p206LtpW1-GUS; FIG. 5(d) pLC-GUS, the promoterless control used in transient assays.

FIG. 6(A–B) shows two prior art constructs used for comparative studies. FIG. 6(a) P35s-GUS, FIG. 6(b) pACT-GUS.

FIG. 7(a) shows *T. aestivum* at 15 dpa; FIG. 5(b) shows *Zea mays* at 13 dpa, and FIG. 7(c) shows *H. vulgare* at 12 dpa.

DESCRIPTION OF PREFERRED EMBODIMENT

Figure 1:
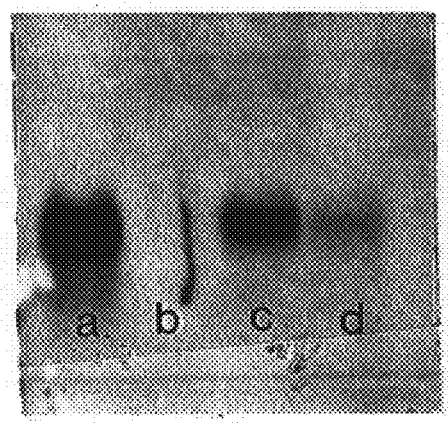
FIG. 1 shows Ltp expression in aleurone tissues of Hordeum and Triticum species using Northern analysis hybridized with a barley Ltp1 DIG-labelled cDNA.

The present invention relates to plant gene regulatory elements and their use in the expression of genes of interest. More specifically, the present invention relates to the use of an aleurone regulatory element for stage and tissue specific expression of a gene of interest within aleurone tissues of plants.

In the context of this disclosure, the term "regulatory element", "regulatory element fragment" or "regulatory element region" refers to a sequence of DNA, usually upstream (5') to the coding sequence of a structural gene, which controls the expression of the coding region by providing the recognition for RNA polymerase and/or other factors required for transcription to start at the correct site. A regulatory element may comprise all, or only one, of the following elements: a promoter, an enhancer, a negative regulatory element (silencer), a translational enhancers, or any other element that mediate gene expression. A regulatory element may also mediate the interaction of other transcriptional factors that regulate promoter activity, either positively or negatively. It is to be understood that a regulatory element may be capable of mediating organ (tissue) specificity, or controlling developmental or temporal gene activation. Furthermore, "regulatory element" includes elements that decrease or increase promoter activity such as negative regulatory elements or enhancers, respectively. It is to be understood that other nucleotide sequences, located within introns, or 3' of the sequence may also contribute to the regulation of expression of a coding region of interest.

Described below is a genomic Ltp sequence obtained from wheat termed LtpWl (SEQ ID NO:4). The coding region of the LtpW1 gene sequence exhibits about an 85% homology with barley Ltp 1, and includes a 26 amino acid transit peptide. The regulatory element of a wheat lipid transfer protein (Ltp) gene, LtpW1, has been isolated and characterized. This regulatory element comprises a novel oligonucleotide sequence (SEQ ID NO: 1), which is active in aleurone of wheat, maize and barley. A restriction map of the full length regulatory element region corresponding to SEQ ID NO: 1 is provided in FIG. 9. The full length regulatory element is not active in leaf, root, or coleoptile tissues. The regulatory element region of LtpW1 compared to the barley Ltp1 promoter has 43% sequence similarity with the majority of sequence similarity (82%) occurring within 140 nucleotides upstream of the transcriptional start site (see FIG. 4(a)). A minor sequence similarity was noted between LtpW1 and a barley amylase protease inhibitor, however, no sequence similarity of any significance was observed between LtpW1 and Ltp2 (FIG. 4(b)), or other known Ltp promoter sequences.

The full length LtpW1 regulatory element (687 nucleotides; p687LtpW1; SEQ ID NO: 1), or a truncated LtpW1 regulatory element, p473LtpW1 (SEQ ID NO:2; comprising a 473 nucleotide fragment of the full length regulatory element or bps 214–687 of SEQ ID NO: 1), can be used to drive the expression of a gene of interest within the aleurone layer of a developing and germinating seed of a monocotyledonous plant, for example, but not limited to, wheat, rice, barley and maize.

Figure 7:
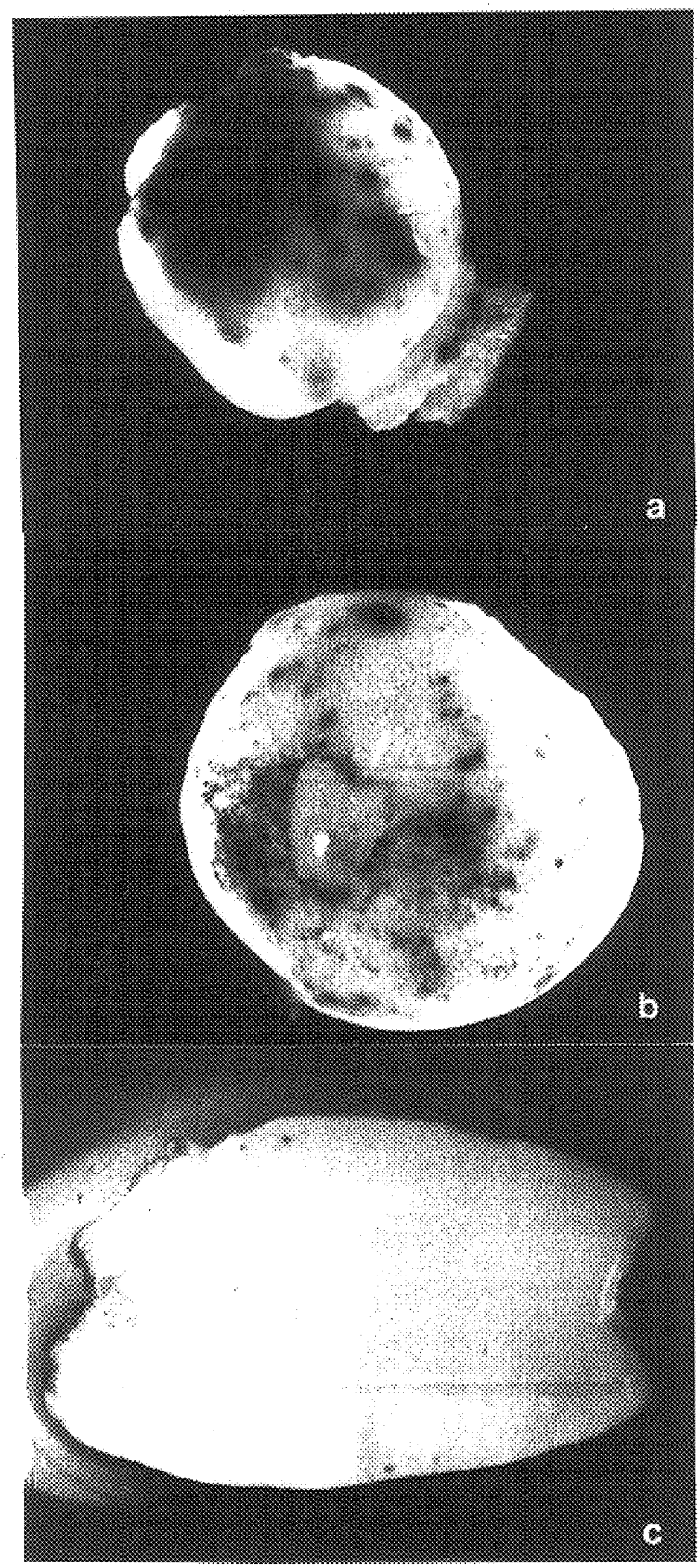
FIG. 7(A–C) shows transient expression of a LtpW1 regulatory element—GUS (p687LtpW1-GUS) fusion in aleurone of cereal grains delivered by microprojectile bombardment.
Figure 8:
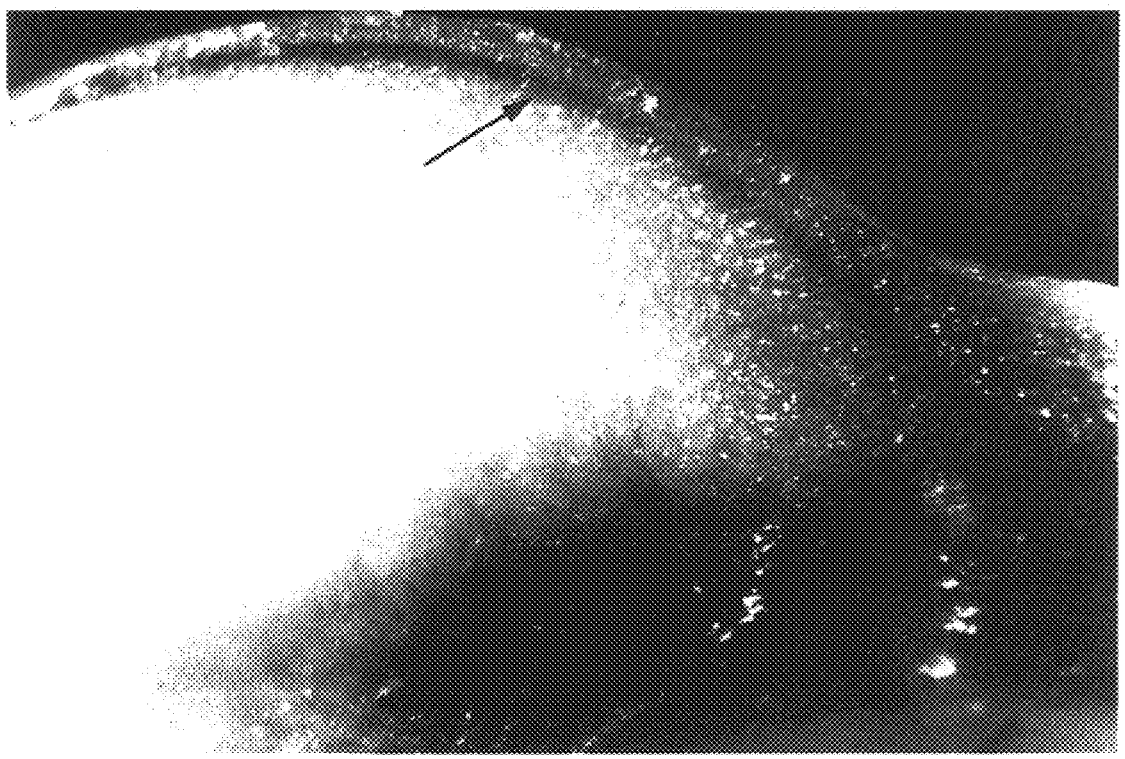
FIG. 8 shows GUS expression in aleurone layer (arrowed) of 3 days germinated kernel of *Z. mays*, T1 self progeny, transformed with p473LtpW1-GUS fusion.

LtpW1 exhibits 8.8% of 35S activity and 12.2% activity of the strong rice action monocot constitutive promoter (Table 2, Example 3). Comparison of histological evidence of expression of Ltp2 (Kalla et al 1994, Plant J. 6:849–860)), with FIG. 7 of the present invention (histological evidence of LtpW1 activity) indicates that LtpW1 is more than two times stronger than Ltp2.

Figure 9:
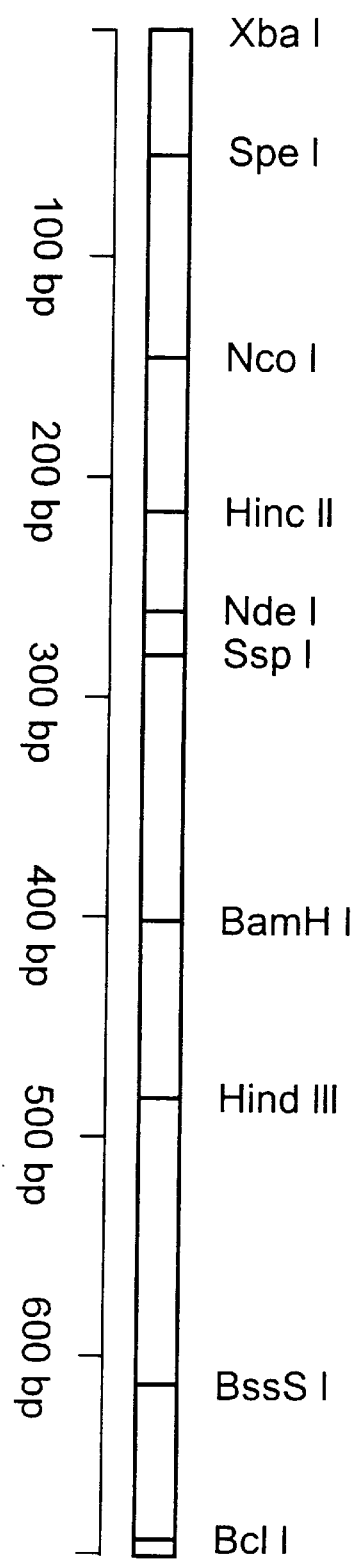
FIG. 9 shows a restriction map of the LtpW1 regulatory element corresponding to the sequence of SEQ ID NO: 1.

Experiments with deletions of the full length LtpW1 regulatory element indicate that a 473 nucleotide fragment (SEQ ID NO: 2; p473LtpW1 or bps 214–687 of SEQ ID NO:1) of the full length regulatory element is more active in aleurone tissue than the 687 base pair fragment, (FIG. 9; SEQ ID NO: 1), p687LtpW1 (Table 3). However, neither the full length regulatory element, nor the 473 bp truncated regulatory element (p 473 ltpW1) were active in leaf tissue (see Table 4). A truncated regulatory element comprising a 206 bp nucleotide fragment (SEQ ID NO:3, p206LtpW1 bps 481–687 of SEQ ID NO:1) of the full length regulatory element was active in aleurone, leaf, and scutellum tissue, functioning as a minimal promoter element. This 206 bp region therefore represents a novel, potentially constitutive, regulatory element for monocotyledonous plants.

The DNA sequences of the present invention thus include the DNA sequences of SEQ ID NO: 1, 2, 3 and 4, the regulatory regions and fragments thereof, as well DNA sequences that are to substantially homologous to the nucleic acids defined in SEQ ID NO's 1, 2, 3 and 4. By substantially homologous it is meant DNA sequences that are analogues of, or nucleic acid sequences comprising at least about 80% similarity with the nucleic acids as defined in SEQ ID NO's: 1, 2, 3, and 4. Analogues include those DNA sequences which hybridize under stringent hybridization conditions (see Maniatis et al., in Molecular Cloning (A Laboratory Manual), Cold Spring Harbor Laboratory, 1982, p. 387–389) to the DNA sequence of SEQ ID NO: 1, 2, 3 or 4, provided that said sequences maintain at least one regulatory property of the activity of the regulatory element as defined herein. An example of one such stringent hybridization condition includes hybridization using 5×SSC and 50% formamide at 42° C., followed by washing in about 0.5×SSC to about 0.2×SSC at 65° C.

The data as presented herein indicate that nucleotides 1–214 and 215–481 of SEQ ID NO: 1 (687 to −473, and −472 to −206 of FIG. 3, respectively) responsible for imparting tissue specificity within this sequence, since once the nucleotides 1–481 (687 to −206 of FIG. 3) are removed from the full length sequence, tissue specificity is lost (Table 4). It is contemplated that either of these regions may be combined with any suitable regulatory element of interest, for example, which is not to be considered limiting, a minimal, constitutive, or viral promoter etc. in order to obtain aleurone-specific expression of a gene linked thereto. Both of these regions (nucleotides 1–214 and 215–481 of SEQ ID NO: 1 (−687 to −473, and −472 to −206 of FIG. 3 respectively)) were found to comprise very low sequence similarity with other sequences present within gene sequence databases such as GenBank.

Furthermore, the data presented in Table 3 indicates that the region comprising nucleotides 1–481 of SEQ ID NO: 1 (−687 to −206 of FIG. 3) is responsible for regulating the strength of promoter activity, and includes both silencer-(negative regulatory element) and enhancer-type activities. For example, the fragment comprising nucleotides 215–481 of SEQ ID NO: 1 (−473 to −206 of FIG. 3) may be used as an enhancer like element as constructs comprising this region (e.g. p473LtpW1) resulted in increased expression when compared with either the full length regulatory element (p687LtpW1) or the truncated regulatory element p206LtpW1 (see Table 3). Similarly, nucleotides 481–687 (−206 to −1, of FIG. 3) also exhibit enhancer-type activity, since constructs comprising this region (p206LtpW1) exhibited higher levels of expression than the full length regulatory element. Therefore, it is contemplated that nucleotides 214–481, or 481–687 (−473 to −206, and −206 to −1 of FIG. 3, respectively) may be combined with any suitable regulatory element of interest, for example, which is not to be considered limiting, a minimal, constitutive, or viral promoter etc., in order to obtain both aleurone-specific expression of a gene linked thereto, as well as increased gene expression.

Similarly, the fragment comprising nucleotides 1–214 (of SEQ ID NO:1, or −687 to −473 of FIG. 3) comprises silencer-type elements as constructs comprising this region (e.g. p687LtpW1) result in lower levels of expression compared with the levels of expression obtained with either of the truncated regulatory element constructs, p206LtpW1, or p473LtpW1 (see Table 3). It is contemplated that nucleotides 1–214 (of SEQ ID NO:1, or −687 to −473 of FIG. 3) may be combined with any suitable regulatory element of interest, for example, which is not to be considered limiting, a minimal, constitutive, or viral promoter etc., in order to obtain both aleurone-specific expression of a gene linked thereto, along with reduced gene expression.

The truncated regulatory element, p473LtpW1, was used to transform maize, where it was noted that this regulatory element was active only in aleurone of developing and germinating cereal grain.

By "constitutive regulatory element" it is meant a regulatory element that directs the expression of a gene throughout the various parts of a plant and continuously throughout plant development. It is not necessary for the level of expression to be the same throughout the different plant parts. Examples of known constitutive regulatory elements include those associated with the CaM35S transcript and Agrobacterium Ti plasmid nopaline synthase gene.

The gene constructs of the present invention can also include other optional regulatory motifs such as enhancers, either translation or transcription enhancers, as may be required. These enhancer regions are well known to persons skilled in the art, and can include, for example, the enhancer region of the 35S regulatory region, as well as other enhancers obtained from other regulatory regions, and/or the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the MRNA.

To aid in identification of transformed plant cells, the constructs of this invention may be further manipulated to include plant selectable markers. Useful selectable markers include, but are not limited to, enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

Also considered part of this invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, embryo or shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, particle bombardment, micro-injection, electroporation, etc, the techniques of which are known to one of skill in the art. For reviews of such techniques see for example Weissbach and Weissbach (1988) and Geierson and Corey (1988).

While not to be considered limiting in any manner, the following examples are provided in order to exemplify embodiments of the present invention.

Example 1

Localization of Ltp1 Expression

In order to isolate genes which are functional in aleurone of developing and germinating wheat grain, a barley cDNA probe of an aleurone specific lipid transfer protein gene (Ltp1,) was used to indicate activity of similar genes in wheat aleurones during seed development. Northern blot analyses using a DIG -labelled barley cDNA probe showed that Ltp transcripts were present in aleurone tissue 20 dpa (FIGS. 1(a) and 1(c)). No activity was detected in early wheat grain development, 10 dpa (FIG. 1(b) but could be detected in *T turgidum* (FIG. 1(d)).

Figure 2:
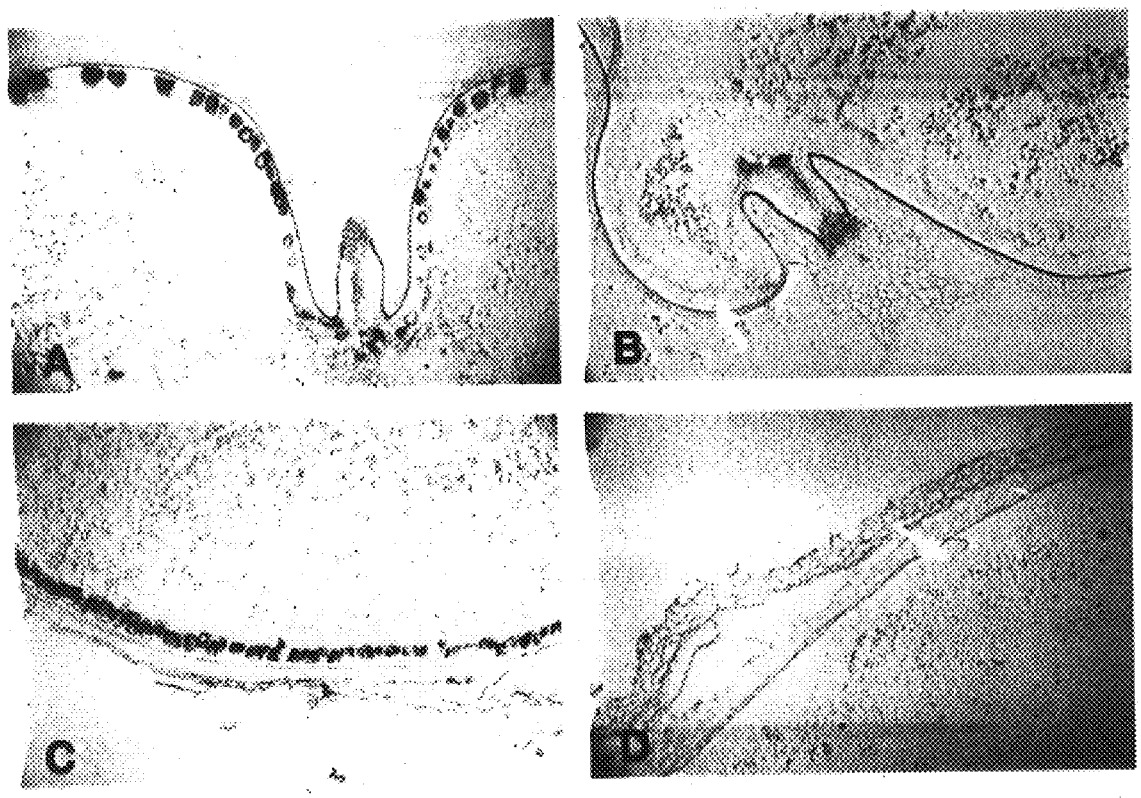
FIG. 2(A–D) shows RNA in situ hybridization of $^{35}$S-labelled barley Ltp ribo-probe in 73h germinating, and 18 dpa developing wheat grain.

In situ hybridization (based on a modification of the procedure outlined in Cox and Goldberg, 1998, Analysis of Plant Gene Expression, In Plant Molecular Biology. A Practical Approach, pp. 1–34) performed on cross sections of developing and germinating grain showed that Ltp expression was limited to aleurone cells. A $^{35}$S Ltp antisense ribo-probe hybridized strongly to aleurone cells (FIG. 2(a)), whereas no differential hybridization was observed with the sense RNA probe (FIG. 2(b)). Ltp expression was observed throughout grain development after 18 dpa and during germination up to 73 h post-imbibition at which time the endosperm was depleted. No hybridization was observed in developing endosperm, embryo or pericarp tissues (data not shown).

Example 2
Genomic DNA of LtpW1

Genomic DNA was isolated from young leaf tissue of hexaploid wheat, (Taestivum) and digested with XbaI. When this DNA was analysed by Southern blot using standard procedures and a DIG-labelled barley Ltp cDNA probe, three loci for the Ltp1 gene (at 1.5, 6.0, and 7.0 kb) were detected. The copy corresponding to the 1.5 kb XbaI band was cloned by screening a λ long C phage library of size-restricted XbaI fragments with a barley Ltp1 cDNA probe. LtpW1 refers to the Ltp gene contained within the 1.5 kb XbaI digested *T. aestivum* genomic clone, the sequence of which is shown in SEQ ID NO: 4 (also see FIG. 3).

The coding sequence of LtpW1 shares 85% DNA identity with the barley Ltp1 (FIG. 4 (a)), includes a 26 amino acid transit peptide for cell wall localization of the protein, and has one predicted 88 bp intron which is 44 bp shorter than the equivalent barley intron. The nucleotide sequences LtpW1 and barley Ltp I promoter (Linnestad 1991) are well conserved for approximately 140 bp upstream of the ATG start codon whereupon they diverge considerably (FIG. 4 (a)). The conserved region includes the putative cap and TATA sites but not the proposed CAT site or other regulatory elements (see FIGS. 3, and 4(a)).

The nucleotide sequence of the LtpW1 regulatory element exhibits little or no identity with the barley Ltp2 promoter (FIG. 4(b)). The LtpW1 regulatory element was shown to be active in aleurone of developing and germinating cereal grain which is uniquely different from the barley Ltp2 regulatory element which is only active during grain development but not during germination (Kalla et al 1994).

Example 3
Expression of GUS under the control of LtpW1 aleurone regulatory elements.

p687LtpW1-GUS

A 687 bp XbaI/BclII regulatory element fragment (SEQ ID NO: 1; FIG. 3) was subcloned from pLtpW1 and fused to a GUS promoterless reporter cassette (pLC-GUS). pLC-GUS was obtained by removing the 35S promoter as a SacI fragment from pZO1016 (designated p35S-GUS herein), which was a gift from R. Sinibaldi, Sandoz, Calif. A 687 bp XbaI/BclII fragment was isolated from pTALP1 (containing the 1.5 kb XbaI-digested *T. aestivum* genomic clone) and the sticky ends were filled-in with Klenow fragment of DNA polymerase. This fragment was blunt-end ligated into the SmaI site of pLCGUS (see FIG. 5(d)), and the orientation of the insert was checked by digesting with BamH1. The activity of this construct was compared with that of the promoterless construct (pLC-GUS) as well as to constructs comprising constitutive CaMV35S and rice actin promoters (see FIGS. 6(a) and (b), respectively). These constructs were used for comparison studies. The 35S promoter is described in: Odel, J. T., Nagy, F. and Chua N-H (1985) Nature 313:810–812. The rice actin promoter is described in: McElroy D., Zhang, W. Cao, J. and Wu, R. (1990) Plant Cell 2:163–171.

These constructs were introduced into the aleurone of cereal grains by microparticle bombardment using standard methods. LUC and GUS constructs were co-bombarded in equimolar amounts and GUS is expressed relative to LUC to minimize variability between reps (shots). LUC activity serves as an internal control for the shot to shot variability.

Tissues, 48 h post-bombardment, were incubated in reaction buffer containing 50 mM NaH$_2$PO$_4$ (pH 7.0), 10 mM EDTA and 1 mM 5-bromo-4-chloro-3-indolyl-B-glucoronide (X-Gluc), 0.5 mMK$_3$[Fe(CN)$_6$], 0.5 mMK$_4$[Fe(CN)$_6$] at 37° C. for 4–20 h. A blue precipitate in the bombarded cells indicates activity of B-glucoronidase. The fall length regulatory element gave high expression of GUS in histological transient assays with wheat aleurones (FIG. 7(a)). Activity was also demonstrated in maize and barley aleurones (FIG. 7(b) and (c)) The 687 bp regulatory element fragment showed no activity in leaf, root or coleoptile tissues of wheat (data not shown).

In quantitative expression assays in wheat aleurone the 687 bp regulatory element had 3.4% of the activity of the constitutive 35S promoter (Table 1). This underestimates the relative aleurone-directed activity of the LtpW1 regulatory element because of additional endosperm-derived activity of the constitutive 35S promoter.

TABLE 1

Activity of p687LtpW1 in 12 dpa wheat aleurone

| Construct | Luciferase (mv/sec/mg/ protein) | GUS (pmol MU/min/mg protein) | GUS/LUC | % 35S Activity |
|---|---|---|---|---|
| Au | 200[1] | 0 | 0 | — |
| pLC-GUS[2]/p35S-LUC | 2100 | 0 | 0 | — |
| p35S-GUS/p35S-LUC | 3400 | 30072 | 8.84 | — |
| p687LtpW1-GUS/p35S-LUC | 4200 | 1247 | 0.30 | 3.4 |

[1]mean of three sets of bombardments
[2]promoterless construct

P473LtpW1-GUS

A truncated version of the LtpW1 regulatory element (see SEQ ID NO:2; FIG. 3) was prepared by digesting pTALTP1 with HincII and BclI, and the resulting 0.47 kb fragment (after treatment with Klenow) was ligated into the SmaI site of pLC-GUS. Orientation of the insert was checked by digesting the resulting recombinant plasmid with BamHI. The construct (p473LtpW1-GUS comprising bps 214–687 of SEQ ID NO:1, or −473 to −1 of FIG. 3) thus obtained showed 8.8% and 12.2% activity of the constitutive 35S and rice actin promoters, respectively (pAct-GUS was a gift from Ray Wu at Cornell). See Table 2 for results.

TABLE 2

Activity of p473LtpW1 in 12 dpa wheat aleurone

| Construct | Luciferase (mv/sec/mg/ protein) | GUS (pmol MU/min/mg protein) | GUS/LUC | % 35S Action Activity |
|---|---|---|---|---|
| Au | 200[1] | 0 | 0 | — |
| pLC-GUS[2]/p35S-LUC | 1300 | 0 | 0 | — |
| p35S-GUS/p35S-LUC | 3500 | 8077 | 2.31 | — |
| pAct-GUS/p35S-LUC | 3300 | 5524 | 1.67 | — |
| p473LtpW1-GUS/p35S-LUC | 3200 | 651 | 0.20 | 8.8 12.2 |

[1]mean of three sets of bombardments
[2]promoterless construct

When compared within a single experiment, the 473 bp fragment (bps 214–687 of SEQ ID NO:1, or –473 to –1 of FIG. 3) was 170% as active as the 687 bp fragment (Table 3).

TABLE 3

Activity of p687LtpW1, p473LtpW1, and p206LtpW1 in 7 dpa wheat aleurone

| Construct | Luciferase (mv/sec/ mg/protein) | GUS (pmol MU/min/mg protein) | GUS/LUC | % 35S Activity |
|---|---|---|---|---|
| pLC-GUS[2]/p35S-LUC | 9700[1] | 120 | 0.01 | 0.1 |
| p35S-GUS/p35S-LUC | 2300 | 18305 | 7.96 | — |
| p206LtpW1-GUS/p35S-LUC | 7900 | 1781 | 0.23 | 2.9 |
| p473LtpW1-GUS/p35S-LUC | 6800 | 2399 | 0.35 | 4.4 |
| p687LtpW1-GUS/p35S-LUC | 5100 | 1090 | 0.21 | 2.6 |

[1]mean of three sets of bombardments
[2]promoterless construct

To generate P206LtpW1-GUS, pTALTP1 was digested with BclI, then with HindIII, and the 0.2 kb fragment was isolated from a gel and purified. The sticky ends were filled in with Klenow and the resulting fragment was ligated into the SmaI site of pLC-GUS. Neither the 687 bp or 473 bp regulatory element was active in leaf tissue, but the 206 bp HinII/BclI truncated regulatory element (SEQ ID NO:3; bps 481–687 of SEQ ID NO:1, or bps –206 to –1 of FIG. 3) had 7.5% the activity of the 35S promoter in leaf (Table 4).

Similarly, in wheat scutellum tissue, only the 206 bp regulatory element fragment was active (Table 5) with activities of 11.4% of 35S and 8.5% of rice actin promoters.

TABLE 4

Activity of p687LtpW1, p473LtpW1, and p206LtpW1 in wheat leaf tissue

| Construct | Luciferase (mv/sec/ mg/protein) | GUS (pmol MU/min/mg protein) | GUS/LUC | % 35S Activity |
|---|---|---|---|---|
| pLC-GUS[2]/p35S-LUC | 200[1] | 1.6 | 0.007 | 0.7 |
| p35S-GUS/p35S-LUC | 200 | 204.3 | 1.020 | — |
| p206LtpW1-GUS/p35S-LUC | 200 | 15.3 | 0.077 | 7.5 |
| p473LtpW1-GUS/p355-LUC | 700 | 1.3 | 0.002 | 0.2 |
| p687LtpW1-GUS/p355-LUC | 700 | 1.7 | 0.002 | 0.2 |

[1]mean of three sets of bombardments
[2]promoterless construct

TABLE 5

Activity of p687LtpW1, p473LtpW1, and p206LtpW1 in 20 dpa wheat scutellum tissue

| Construct | Luciferase (v/sec/ mg/protein) | GUS (pmol MU/min/mg protein) | GUS/LUC | % 35S Action Activity |
|---|---|---|---|---|
| pLC-GUS[2]/p35S-LUC | 1300[1] | 37 | 0.028 | 0.23, 0.17 |
| p35S-GUS/p35S-LUC | 400 | 4873 | 12.182 | — |
| pAct-GUS/p35S-LUC | 400 | 6530 | 16.325 | — |
| p206LtpW1-GUS/p35S-LUC | 100 | 139 | 1.39 | 11.41, 8.51 |
| p473LtpW1-GUS/p35S-LUC | 200 | 2 | 0.01 | 0.08, 0.06 |
| p687LtpW1-GUS/p35S-LUC | 200 | 6 | 0.03 | 0.24, 0.18 |

[1]mean of three sets of bombardments
[2]promoterless construct

Thus the nucleotide sequence between 206 bp and 473 bp (i.e. −206 to −473 of FIG. 3, or 418–214 of SEQ ID NO:1) determines the tissue (organ) and stage dependent (temporal) regulation of the LtpW1 regulatory element.

Collectively, these data indicate that:

nucleotides 1–214 of SEQ ID NO:1 (i.e. the portion of the promoter between p687LtpW1 to p473LtpW1, bps −687 to −473 of FIG. 3) and 215–481 of SEQ ID NO:1 (bps −472 to −206 of FIG. 3) are responsible for imparting tissue specificity. Removal of either of these regions from the full length regulatory element results in greatly reduced tissue specificity (Table 4).

the region comprising nucleotides 1–481 of SEQ ID NO: 1 (bps −687 to −206 of FIG. 3) is responsible for regulating the strength of regulatory element activity, and includes both silencer- and enhancer-type activities:

the fragment comprising nucleotides 214–481 of SEQ ID NO:1 (bps −473 to −206 of FIG. 3) exhibits enhancer-like activity as constructs comprising this region (e.g. p473LtpW1) resulted in increased expression when compared with either the full length regulatory element (p687LtpW1), or the truncated fragment p206LtpW1 (see Table 3). Similarly, nucleotides 482–687 of SEQ ID NO:1 (bps −205 to −1 of FIG. 3) also exhibit enhancer-type activity, since constructs comprising this region (p206LtpW1) exhibited higher levels of expression than the full length regulatory element;

the fragment comprising nucleotides 1–214 of SEQ ID NO:1 (bps −687 to −473 of FIG. 3) comprises silencer-type elements as constructs comprising this region (e.g. p687LtpW1) result in lower levels of expression compared with the levels of expression obtained with either of the truncated constructs, p206LtpW1, or p473LtpW1 (see Table 3);

the 206 bp version of the full length regulatory element (i.e. 481–687 of SEQ ID NO:1, or bps −206 to −1 of FIG. 3) represents a novel constitutive promoter for monocotyledonous plants.

Because of the relatively superior activity of the 473 bp fragment (i.e. 214–687 of SEQ ID NO:1, or bps −473 to −1 of FIG. 3) in aleurone tissue (Tables 1,2 and 3), this version was used for transformation of maize.

Example 4

Preparation of transgenic plants of *Zea mays*

To verify that the 5' flanking sequence from the genomic clone LtpW1 contained the regulatory sequences required to confer expression in aleurone cells, the 473 bp LtpW1 /GUS fusion was co-bombarded with a bialaphos selectable plasmid (pAHC25) into embryogenic cultures of maize. Transgenic calli were selected on bialaphos media and transgenic plants regenerated. The transgenic plants were screened for GUS activity. The 473 bp LtpW1 regulatory element directed the expression of GUS only in the aleurone layer of developing and germinating transgenic maize kernels (FIG. 6).

The present invention has been described with regard to preferred embodiments. However, it will be obvious to persons skilled in the art that a number of variations and modifications can be made without departing from the scope of the invention as described herein.

We claim:

1. An isolated DNA molecule that hybridizes to the nucleotide sequence of SEQ ID NO: 1 under the following conditions: hybridization in 5×SSC and 50% formamide at 42° C., and washing in from about 0.5×SSC to about 0.2×SSC at 65 ° C. wherein said DNA molecule exhibits the regulatory element activity of SEQ ID NO:1.

2. The isolated DNA molecule of claim 1 comprising at least 40 contiguous nucleotides of the nucleotide sequence of SEQ ID NO: 1, wherein said isolated DNA molecule exhibits the regulatory element activity.

3. The isolated DNA molecule of claim 1 comprising at least 21 contiguous nucleotides of the nucleotide sequence comprising nucleotides 1–481 of SEQ ID NO: 1. wherein said isolated DNA molecule exhibits the regulatory element activity of nucleotides 1–481 of SEQ ID NO:1.

4. The isolated DNA molecule of claim 1 comprising at least 19 contiguous nucleotides of the nucleotide sequence comprising nucleotides 1–214 of SEQ ID NO: 1, wherein said isolated DNA molecule exhibits regulatory element activity of nucleotides 1–214 of SEQ ID NO:1.

5. The isolated DNA molecule of claim 1 comprising the nucleotide sequence of SEQ ID NO:1.

6. An isolated DNA molecule that hybridizes to the nucleotide sequence of SEQ ID NO:2 under the following conditions: hybridization in 5×SSC and 50% formamide at 42° C.; and washing in from about 0.5×SSC to about 0.2×SSC at 65° C., wherein said DNA molecule exhibits the regulatory element activity of SEQ ID NO:2.

7. The isolated DNA molecule of claim 6 comprising the nucleotide sequence of SEQ ID NO.2.

8. An isolated DNA molecule that hybridizes to the nucleotide sequence of SEQ ID NO:3 under the following conditions: hybridization in 5×SSC and 50% formamide at 42° C.; and washing in from about 0.5×SSC to about 0.2×SSC at 65° C. wherein said DNA molecule exhibits the regulatory element activity of SEQ ID NO:3.

9. The isolated DNA molecule of claim 8 comprising the nucleotide sequence of SEQ ID NO:3.

10. The isolated DNA molecule of claim 3 comprising nucleotides 1–481 of the nucleotide sequence of SEQ ID NO: 1.

11. The isolated DNA molecule of claim 4 comprising nucleotides 1–214 of the nucleotide sequence of SEQ ID NO: 1.

12. The isolated DNA molecule of claim 2 comprising nucleotides 215–481 of the nucleotide sequence of SEQ ID NO: 1.

13. A vector comprising the isolated DNA molecule of claim 1 and a gene of interest operatively linked thereto, wherein said isolated DNA molecule controls the expression of said gene of interest.

14. A transformed plant cell culture comprising the vector of claim 13.

15. A transgenic plant transformed with the vector of claim 13.

16. A method of expressing a gene of interest within aleurone of a plant comprising:

i) operatively linking a gene of interest for which expression is desired with a regulatory element obtained from wheat aleurone, to produce a chimeric gene construct; and ii) introducing the chimeric gene construct into said plant and allowing for expression of said gene of interest;

wherein said regulatory element comprises the nucleotide sequence as defined by claim 1.

17. A method of expressing a gene of interest within alcurone of a plant comprising:

i) operatively linking a gene of interest for which expression is desired with a regulatory element obtained from wheat aleurone, to produce a chimeric gene construct; and ii) introducing the chimeric gene construct into said plant and allowing for expression of said gene of interest;

wherein said regulatory element comprises the nucleotide sequence as defined by claim 6.

18. A method of expressing a gene of interest within alcurone of a plant comprising:

i) operatively linking a gene of interest for which expression is desired with a regulatory element obtained from wheat aleurone, to produce a chimeric gene construct; and ii) introducing the chimeric gene construct into said plant and allowing for expression of said gene of interest;

wherein said regulatory element comprises the nucleotide sequence as defined by claim 8.

19. A vector comprising the isolated DNA molecule of claim 1.

20. An expression vector comprising the isolated DNA molecule of claim 1 operably linked to DNA encoding a protein.

21. A vector comprising the isolated DNA molecule of claim 6.

22. An expression vector comprising the isolated DNA molecule of claim 6 operably linked to DNA encoding a protein.

23. A vector comprising the isolated DNA molecule of claim 8.

24. An expression vector comprising the isolated DNA molecule of claim 8 operably linked to DNA encoding a protein.

* * * * *

UNITED STATES PATENT AND TRADEMARK OFFICE
CERTIFICATE OF CORRECTION

PATENT NO. : 6,013,862
DATED : Janaury 11, 2000
INVENTOR(S) : John SIMMONDS et al It is certified that error appears in the above-indentified patent and that said Letters Patent is hereby corrected as shown below:

Title page, item, [73], Assignee should read --Her Majesty in Right of Canada as Represented by the Minister of Agriculture and Agri-Food Canada, Ontario, Canada--.

Column 2, line 30, "Lpt2" should read --Ltp2--;
  line 32, "Lpt" should read --Ltp--;
  line 50 "finctioning" should read --functioning--
Column 3, line 33 "HincIII" should read --HincII--;
Column 5, line 30 "P35s" should read --p35S--;
  line 61 "a translational enhancers" should read --translational enhancers--;
Column 6, line 63 "that are to substantially homologous" should read --that are substantially homologous--;
Column 7, line 15 "respectively) responsible" should read --respectively), are responsible--;
Column 8, line 23 "MRNA" should read --mRNA--;
Column 10, line 30 "fall" should read --full--
  line 59 "BelI" should read --BeII--
Column 11, Table 2, right hand column heading, "%35S Action Activity" should read --%35S Actin Activity--
  line 42 "687 bp or 473 bp" should read --687 bp nor 473 bp--
  line 44 "HinII/BclI" should read --HindIII/BcII--
Column 13, Table 5, right hand column "%35 Action Activity should read --%35S Actin activity--
  line 25 "215-481 and SEQID" should read --215-481 of SEQ ID--.

UNITED STATES PATENT AND TRADEMARK OFFICE
CERTIFICATE OF CORRECTION

PATENT NO. : 6,013,862
DATED : Janaury 11, 2000
INVENTOR(S) : John SIMMONDS et al It is certified that error appears in the above-indentified patent and that said Letters Patent is hereby corrected as shown below:

Column 20, line 25 (claim 17, line 2) "alcurone" should read --aleurone-- and
line 36 (claim 18, line 2) "alcurone" should read --aleurone--

Signed and Sealed this

Twenty-seventh Day of March, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.    : 6,013,862
DATED         : January 11, 2000
INVENTOR(S)   : John Simmonds et al.

It is certified that error appears in the above-identified patent and that said Letters Patent is hereby corrected as shown below:

<u>Title page,</u>
Item [73], Assignee should read -- Her Majesty in right of Canada as represented by the Minister of Agriculture and Agri-Food Canada --.

Signed and Sealed this

Second Day of October, 2001

Attest:

NICHOLAS P. GODICI
Attesting Officer    Acting Director of the United States Patent and Trademark Office